(12) United States Patent
Kendrick et al.

(10) Patent No.: US 12,171,956 B2
(45) Date of Patent: Dec. 24, 2024

(54) WETTING MECHANISM FOR A CATHETER

(71) Applicant: CONVATEC LIMITED, Flintshire (GB)

(72) Inventors: Andrew Kendrick, Cheshire (GB); Julie Lambrethsen, Cheshire (GB); Oliver Walter Pfleger, Liverpool (GB); Michal Weber, Cheshire (GB); Marian Novak, Trebisov (SK); Lukas Kandrac, Humenne (SK)

(73) Assignee: CONVATEC LIMITED, Flintshire (GB)

( * ) Notice: Subject to any disclaimer, the term of this patent is extended or adjusted under 35 U.S.C. 154(b) by 560 days.

(21) Appl. No.: 17/238,333

(22) Filed: Apr. 23, 2021

(65) Prior Publication Data

US 2021/0346648 A1     Nov. 11, 2021

Related U.S. Application Data

(63) Continuation of application No. PCT/GB2021/050979, filed on Apr. 23, 2021.

(30) Foreign Application Priority Data

Apr. 24, 2020 (GB) ...................... 2006059

(51) Int. Cl.
*A61M 25/01* (2006.01)
*A61M 25/00* (2006.01)

(52) U.S. Cl.
CPC ....... *A61M 25/0111* (2013.01); *A61M 25/002* (2013.01); *A61M 25/0075* (2013.01); *A61M 2025/0078* (2013.01)

(58) Field of Classification Search
CPC ............ A61M 25/002; A61M 25/0111; A61M 25/0017; A61M 25/0113;
(Continued)

(56) References Cited

U.S. PATENT DOCUMENTS

| 5,460,616 | A  | * | 10/1995 | Weinstein | ......... | A61M 39/0606 |
| | | | | | | 604/167.03 |
| 8,240,335 | B1 | * | 8/2012 | Broberg | .............. | F16K 11/0716 |
| | | | | | | 137/625.48 |

(Continued)

FOREIGN PATENT DOCUMENTS

| EP | 3459583 A1 | 3/2019 |
| EP | 3283136 B1 | 6/2021 |

(Continued)

OTHER PUBLICATIONS

International Search Report; European Patent Office; International Application No. PCT/GB2021/050979; Aug. 10, 2021; 3 pages.
(Continued)

*Primary Examiner* — Adam Marcetich
(74) *Attorney, Agent, or Firm* — TAFT STETTINIUS HOLLISTER LLP; Ryan O. White; Derek B. Lavender

(57) ABSTRACT

The invention relates to a wetting mechanism 20 for wetting a tube 12 of a catheter 10. The wetting mechanism 20 includes a housing 16 to be positioned at or proximal to the tip end 13 of the catheter tube 12, where the housing 16 comprises a holding chamber 22 and a wetting chamber 23. The wetting mechanism 20 comprises a fluid release control component 26 for controlling release of fluid within the holding chamber 22 into the wetting chamber 23. At least a portion of the catheter tube 12 is then able to be introduced and be moved through the wetting chamber 23 to wet the catheter tube 12, in use.

12 Claims, 8 Drawing Sheets

(58) Field of Classification Search
CPC .. A61M 2210/1089; A61M 2210/1085; A61M 2210/1096; A61M 2210/1092; A61M 2025/0018; A61M 2202/0496; A61M 25/0075; A61M 25/01; A61M 2039/062; A61M 2210/1078; F16K 11/16; F16K 11/161; F16K 11/065; F16K 11/07; F16K 11/0704; F16K 11/0708; F16K 11/0712; F16K 11/0716

See application file for complete search history.

(56) References Cited

U.S. PATENT DOCUMENTS

| | | | |
|---|---|---|---|
| 11,376,395 | B2 | 7/2022 | Montes de Oca et al. |
| 11,420,016 | B2 | 8/2022 | Palmer |
| 11,420,017 | B2 | 8/2022 | Hilton et al. |
| 11,497,886 | B2 | 11/2022 | Nielsen et al. |
| 11,524,097 | B2 | 12/2022 | Sellers et al. |
| 11,529,439 | B2 | 12/2022 | O'Mahony et al. |
| 11,534,573 | B2 | 12/2022 | Hannon et al. |
| 11,534,577 | B2 | 12/2022 | House |
| 11,690,947 | B2 | 7/2023 | Gobel |
| 11,724,008 | B2 | 8/2023 | Lundahl et al. |
| 11,730,557 | B2 | 8/2023 | O'Flynn et al. |
| 11,730,918 | B2 | 8/2023 | Farrell et al. |
| 11,738,169 | B2 | 8/2023 | Hickmott et al. |
| 11,771,584 | B2 | 10/2023 | Becker |
| 11,779,727 | B2 | 10/2023 | Eriksson et al. |
| 11,813,412 | B2 | 11/2023 | O'Flynn et al. |
| 11,833,274 | B2 | 12/2023 | Rostami et al. |
| 2009/0024111 | A1 | 1/2009 | Borodulin et al. |
| 2013/0167960 | A1* | 7/2013 | Pethe ............ F16K 3/262 29/890.124 |
| 2015/0173937 | A1* | 6/2015 | Jackson ........... A61F 5/4405 604/328 |
| 2016/0022959 | A1 | 1/2016 | Schertiger et al. |
| 2017/0321404 | A1* | 11/2017 | Wiwi ............... F16K 3/0281 |
| 2018/0078700 | A1 | 3/2018 | Eliasson |
| 2018/0099318 | A1* | 4/2018 | Wiwi ............... B08B 9/055 |
| 2018/0104447 | A1 | 4/2018 | Madlung et al. |
| 2018/0369474 | A1 | 12/2018 | Falleboe et al. |
| 2019/0105462 | A1 | 4/2019 | Schertiger |
| 2019/0201659 | A1 | 7/2019 | Gustavsson et al. |
| 2020/0155261 | A1 | 5/2020 | OFlynn et al. |
| 2020/0222659 | A1 | 7/2020 | Schertiger et al. |
| 2021/0162180 | A1 | 6/2021 | Gershbaum |
| 2021/0196923 | A1 | 7/2021 | Palmer |
| 2021/0228836 | A1 | 7/2021 | Terry |
| 2021/0260332 | A1 | 8/2021 | Panesar et al. |
| 2021/0275727 | A1 | 9/2021 | Farrell et al. |
| 2021/0290895 | A1 | 9/2021 | Nielsen et al. |
| 2021/0330929 | A1 | 10/2021 | Kendrick et al. |
| 2021/0330938 | A1 | 10/2021 | Kendrick et al. |
| 2021/0346644 | A1 | 11/2021 | Kendrick et al. |
| 2021/0346647 | A1 | 11/2021 | Kendrick et al. |
| 2021/0346648 | A1 | 11/2021 | Kendrick et al. |
| 2021/0353449 | A1 | 11/2021 | Sharma et al. |
| 2021/0370019 | A1 | 12/2021 | Erbey et al. |
| 2022/0001136 | A1 | 1/2022 | Hede et al. |
| 2022/0001139 | A1 | 1/2022 | Eriksson et al. |
| 2022/0008626 | A1 | 1/2022 | Farrell et al. |
| 2022/0023585 | A1 | 1/2022 | Schertiger et al. |
| 2022/0054295 | A1 | 2/2022 | Becker |
| 2022/0118161 | A1 | 4/2022 | Bager et al. |
| 2022/0126057 | A1 | 4/2022 | Eriksson et al. |
| 2022/0133426 | A1 | 5/2022 | OFlynn et al. |
| 2022/0134054 | A1 | 5/2022 | Schertiger et al. |
| 2022/0176068 | A1 | 6/2022 | Pfleger et al. |
| 2022/0176069 | A1 | 6/2022 | Jenco et al. |
| 2022/0211973 | A1 | 7/2022 | Palmer |
| 2022/0226602 | A1 | 7/2022 | Farrell |
| 2022/0226604 | A1 | 7/2022 | Murray et al. |
| 2022/0233808 | A1 | 7/2022 | Farrell et al. |
| 2022/0241549 | A1 | 8/2022 | Murray et al. |
| 2022/0241553 | A1 | 8/2022 | Farrell et al. |
| 2022/0249805 | A1 | 8/2022 | Pedersen |
| 2022/0280751 | A1 | 9/2022 | Farrell et al. |
| 2022/0288350 | A1 | 9/2022 | Montes de Oca et al. |
| 2022/0347354 | A1 | 11/2022 | Sileika et al. |
| 2022/0347430 | A1 | 11/2022 | Pedersen |
| 2022/0370688 | A1 | 11/2022 | Sileika et al. |
| 2022/0370689 | A1 | 11/2022 | Sileika et al. |
| 2022/0379075 | A1 | 12/2022 | Hilton et al. |
| 2022/0387673 | A1 | 12/2022 | Farrell et al. |
| 2022/0409859 | A1 | 12/2022 | Sileika et al. |
| 2023/0241288 | A1 | 8/2023 | O'Mahony et al. |
| 2023/0390464 | A1 | 12/2023 | Farrell et al. |

FOREIGN PATENT DOCUMENTS

| | | | |
|---|---|---|---|
| EP | 3854427 | A1 | 7/2021 |
| EP | 3854438 | A1 | 7/2021 |
| EP | 3338827 | B1 | 8/2021 |
| EP | 3862031 | A1 | 8/2021 |
| EP | 3519031 | B1 | 9/2021 |
| EP | 2750749 | B1 | 10/2021 |
| EP | 3184140 | B1 | 10/2021 |
| EP | 3668555 | B1 | 10/2021 |
| EP | 3727550 | B1 | 10/2021 |
| EP | 3892320 | A1 | 10/2021 |
| EP | 3897480 | A1 | 10/2021 |
| EP | 3921009 | A1 | 12/2021 |
| EP | 3930815 | A1 | 1/2022 |
| EP | 3932438 | A1 | 1/2022 |
| EP | 3943140 | A1 | 1/2022 |
| EP | 3952973 | A1 | 2/2022 |
| EP | 3955863 | A1 | 2/2022 |
| EP | 3082929 | B1 | 3/2022 |
| EP | 3983023 | A1 | 4/2022 |
| EP | 3725355 | B1 | 5/2022 |
| EP | 3990084 | A1 | 5/2022 |
| EP | 3990085 | A1 | 5/2022 |
| EP | 3991773 | A1 | 5/2022 |
| EP | 3727549 | B1 | 6/2022 |
| EP | 4015008 | A1 | 6/2022 |
| EP | 2515988 | B2 | 7/2022 |
| EP | 2968842 | B1 | 7/2022 |
| EP | 3897766 | B1 | 7/2022 |
| EP | 4021549 | A1 | 7/2022 |
| EP | 3593850 | B1 | 9/2022 |
| EP | 3821934 | B1 | 9/2022 |
| EP | 4051328 | A1 | 9/2022 |
| EP | 4051329 | A1 | 9/2022 |
| EP | 4051330 | A1 | 9/2022 |
| EP | 4051358 | A1 | 9/2022 |
| EP | 4061463 | A1 | 9/2022 |
| EP | 3257546 | B1 | 10/2022 |
| EP | 4085962 | A1 | 11/2022 |
| EP | 4088749 | A1 | 11/2022 |
| EP | 2688629 | B1 | 12/2022 |
| EP | 3308823 | B1 | 12/2022 |
| EP | 3793626 | B1 | 12/2022 |
| EP | 4101492 | A1 | 12/2022 |
| EP | 2908898 | B1 | 7/2023 |
| EP | 3148625 | B1 | 7/2023 |
| EP | 3651844 | B1 | 7/2023 |
| EP | 3119464 | B2 | 8/2023 |
| EP | 3921009 | B1 | 8/2023 |
| EP | 3990085 | B1 | 8/2023 |
| EP | 3421071 | B1 | 9/2023 |
| EP | 3883630 | B1 | 9/2023 |
| EP | 4241818 | A2 | 9/2023 |
| EP | 4245349 | A2 | 9/2023 |
| EP | 3040097 | B2 | 10/2023 |
| EP | 3299056 | B2 | 10/2023 |
| EP | 3041560 | B1 | 11/2023 |
| EP | 3419681 | B1 | 11/2023 |
| EP | 3721910 | B1 | 11/2023 |
| EP | 4138970 | B1 | 11/2023 |
| EP | 4138972 | B1 | 11/2023 |
| EP | 4268859 | A2 | 11/2023 |
| EP | 4255546 | B1 | 3/2024 |
| GB | 2540125 | B | 1/2017 |
| GB | 2596593 | A | 1/2022 |

(56) References Cited

FOREIGN PATENT DOCUMENTS

| KR | 1020160092786 A | 8/2016 |
|----|----|----|
| WO | 2021183718 A1 | 9/2021 |
| WO | 2021219188 A1 | 11/2021 |
| WO | 2021228341 A1 | 11/2021 |
| WO | 2021231724 A1 | 11/2021 |
| WO | 2021240266 A1 | 12/2021 |
| WO | 2021242487 A1 | 12/2021 |
| WO | 2021242676 A1 | 12/2021 |
| WO | 2021242745 A1 | 12/2021 |
| WO | 2022002483 A1 | 1/2022 |
| WO | 2022003619 A1 | 1/2022 |
| WO | 2022031550 A1 | 2/2022 |
| WO | 2022090055 A1 | 5/2022 |
| WO | 2022108750 A1 | 5/2022 |
| WO | 2022118010 A1 | 6/2022 |
| WO | 2022118011 A1 | 6/2022 |

OTHER PUBLICATIONS

Written Opinion of the International Searching Authority; International Application No. PCT/GB2021/050979; Aug. 10, 2021; 6 pages.

* cited by examiner

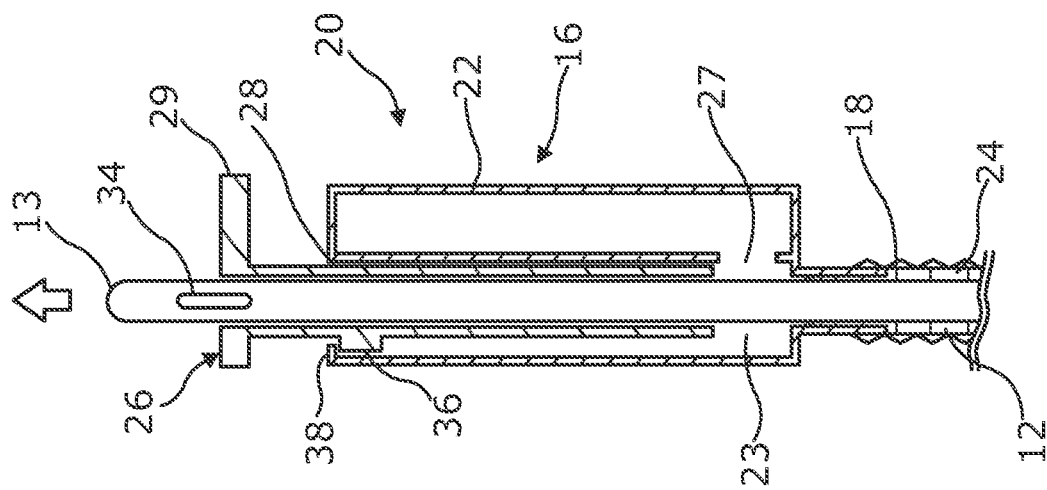
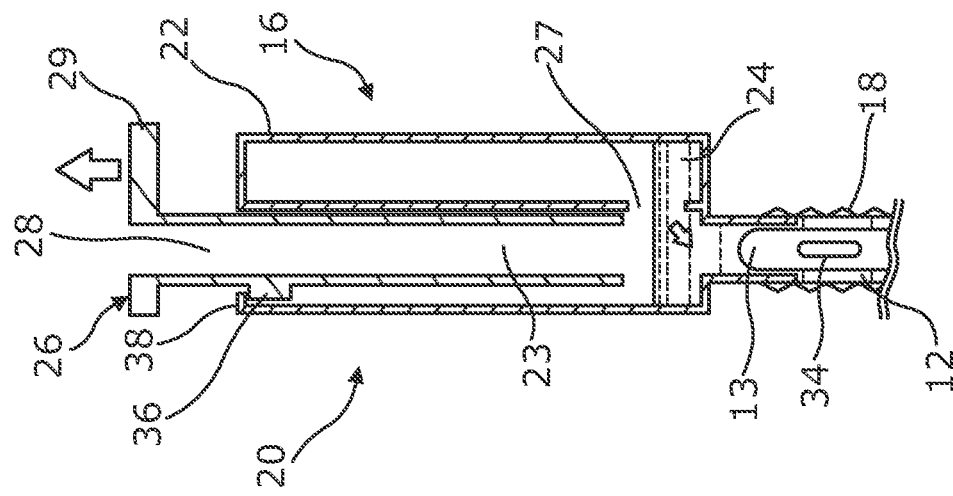
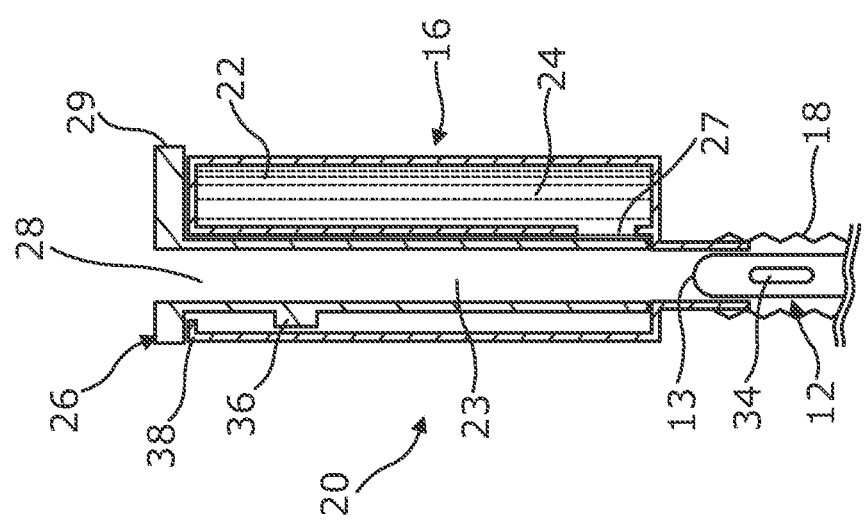

WETTING MECHANISM FOR A CATHETER

This application is a continuation of International Application No. PCT/GB2021/050979 filed Apr. 23, 2021 and claims the priority of GB Application No. 2006059.6, filed Apr. 24, 2020. The disclosures of which are hereby incorporated herein in their entirety.

TECHNICAL FIELD OF THE INVENTION

The present invention relates to a wetting mechanism for a catheter (e.g. a urinary catheter) for wetting a tube of the catheter, in use. The invention extends to a catheter comprising the wetting mechanism and a method for wetting a catheter tube.

BACKGROUND TO THE INVENTION

A catheter is a medical device comprising a hollow catheter tube designed for insertion into canals, vessels, passageways or body cavities to permit injection, drainage or withdrawal of fluids or substances therefrom, or to ensure said canals, vessels, passageways etc. remain open. Urinary catheters are designed for use for insertion into a user's bladder via the urethra to drain the bladder.

To maximise comfort and minimise the risk of trauma and/or infection, an outer surface of the catheter tube is typically wetted using a wetting fluid prior to insertion by the user. In further developments, the catheter tube itself comprises, is integrated with or is coated with a hydrophilic component (e.g. a hydrophilic polymer) which serves to reduce friction further upon application of the wetting fluid.

Some catheters may be supplied pre-wetted in a packaging, for instance, where the catheter is at least partially submerged within wetting fluid within the packaging. However, such arrangements suffer in that components of the catheter other than the catheter tube such as a gripper element or funnel can also become wetted. This has a detrimental effect of the experience of the user where it may become difficult to hold and direct the catheter tube as required. This is particularly problematic where the user is performing self-catheterisation. Further, having the catheter submerged may effectively reduce the shelf-life of the catheter due to long-term exposure of components of the catheter to moisture.

It is therefore seen advantageous to provide a catheter which may be wetted at or immediately prior to the point of use.

In an attempt to address this, some catheters are provided in packaging which includes a rupturable container or sachet within the packaging which a user may burst to release the wetting fluid. Typically, this involves the user squeezing the packaging to cause the container/sachet to break. However, such arrangements experience similar problems to those discussed above where the wetting fluid is allowed to come into contact with other components of the catheter.

It would therefore be advantageous to provide a catheter which includes a means of supplying a wetting fluid solely to the catheter tube to improve user experience.

It is an aim of an embodiment or embodiments of the invention to overcome or at least partially mitigate one or more problems with the prior art.

SUMMARY OF THE INVENTION

According to an aspect of the invention there is provided a wetting mechanism for wetting a tube of a catheter, the wetting mechanism comprising a housing having: a holding chamber for containing a volume of fluid therein; and a wetting chamber into which at least a portion of the catheter tube is able to be introduced and be moved therethrough; and wherein the wetting mechanism comprises a fluid release control component for controlling release of the fluid from the holding chamber to the wetting chamber.

According to an aspect of the invention there is provided a wetting mechanism for wetting a tube of a catheter, the wetting mechanism comprising: a housing configured to be positioned initially at or proximal to the tip end of the catheter tube, and wherein the housing comprises: a holding chamber for containing a volume of fluid therein; and a wetting chamber into which at least a portion of the catheter tube is able to be introduced and be moved therethrough to move at least a portion of the catheter tube through the wetting chamber, in use; and wherein the wetting mechanism comprises a fluid release control component for controlling release of the fluid from the holding chamber to the wetting chamber.

Advantageously, controlling the release of the fluid from a holding chamber where it is held out of contact with other components of the catheter system overcomes issues with the prior art, particularly where catheters may be disadvantageously submerged in wetting fluid prior to use. It may also improve the shelf life of the catheter by reducing the exposure of most of the components of the catheter to moisture until (or as close as possible to) the point of use. Further, controlling the release of the wetting fluid into a wetting chamber through which the catheter tube may be moved through provides greater control over the application of the wetting fluid to the external surface of the catheter tube. This may ensure the whole surface of the catheter tube is adequately wetted prior to use by the user.

Optional features set out below may apply to any aspect of the invention as appropriate.

The fluid release control component may comprise a first configuration wherein it prevents release of the fluid from the holding chamber to the wetting chamber. The fluid release control component may comprise a second configuration wherein it allows release of the fluid from the holding chamber to the wetting chamber. The fluid release control component may be moveable between the first and second configurations. For example, in some embodiments the fluid release control component may be linearly moveable between the first and second configurations. In other embodiments the fluid release control component may be operable to rotate between first and second configurations for controlling the flow of fluid from the holding chamber to the wetting chamber.

In some embodiments the fluid release control component comprises a plug. The plug may be linearly moveable within the wetting mechanism between first and second positions. The plug may be rotatable between first and second angular positions. For example, the plug may be threaded, and may be provided within the wetting mechanism through interaction with a complementary threaded surface of the wetting mechanism. The first and second (optionally angular) positions of the plug may correspond to first and second configurations of the fluid release control component.

One particularly preferred embodiment provides a wetting mechanism for wetting a tube of a catheter, the wetting mechanism comprising: a housing configured to be positioned initially at or proximal to the tip end of the catheter tube, and wherein the housing comprises: a holding chamber for containing a volume of fluid therein; and a wetting chamber into which at least a portion of the catheter tube is able to be introduced and be moved therethrough to move at least a portion of the catheter tube through the wetting chamber, in use; and wherein the wetting mechanism comprises a fluid release control component for controlling release of the fluid from the holding chamber to the wetting chamber; wherein the fluid release control component comprises a first configuration wherein it prevents release of the fluid from the holding chamber to the wetting chamber and a second configuration wherein it allows release of the fluid from the holding chamber to the wetting chamber; wherein the fluid release control component comprises a plug which is linearly moveable within the wetting mechanism between first and second positions corresponding to first and second configurations of the fluid release control component.

In embodiments, the plug may be configured to be at least partly withdrawn from the wetting mechanism. The plug may, at least initially be positioned within the wetting chamber of the wetting mechanism. In such embodiments, the plug may be configured to be at least partly withdrawn from the wetting chamber to cause release of the fluid from the holding chamber into the wetting chamber. The plug may be configured to be only partly withdrawn from the wetting mechanism—i.e. it cannot be fully withdrawn from the wetting mechanism. It may remain attached or otherwise coupled to the housing whether in the first or second position. In further embodiments, the plug may be configured such that it can be fully withdrawn from the wetting mechanism. For example, in some embodiments the plug may initially be positioned within the wetting chamber and may be fully withdrawn from the wetting chamber, in use, to cause release of the fluid from the holding chamber to the wetting chamber.

Another particularly preferred embodiment provides a wetting mechanism for wetting a tube of a catheter, the wetting mechanism comprising: a housing configured to be positioned initially at or proximal to the tip end of the catheter tube, and wherein the housing comprises: a holding chamber for containing a volume of fluid therein; and a wetting chamber into which at least a portion of the catheter tube is able to be introduced and be moved therethrough to move at least a portion of the catheter tube through the wetting chamber, in use; and wherein the wetting mechanism comprises a fluid release control component for controlling release of the fluid from the holding chamber to the wetting chamber; wherein the fluid release control component comprises a first configuration wherein it prevents release of the fluid from the holding chamber to the wetting chamber and a second configuration wherein it allows release of the fluid from the holding chamber to the wetting chamber; wherein the fluid release control component comprises a plug which is linearly moveable within the wetting mechanism between first and second positions corresponding to first and second configurations of the fluid release control component; wherein the plug is configured to be at least partly withdrawn from the wetting mechanism to cause release of fluid from the holding chamber into the wetting chamber.

Another particularly preferred embodiment provides a wetting mechanism for wetting a tube of a catheter, the wetting mechanism comprising: a housing configured to be positioned initially at or proximal to the tip end of the catheter tube, and wherein the housing comprises: a holding chamber for containing a volume of fluid therein; and a wetting chamber into which at least a portion of the catheter tube is able to be introduced and be moved therethrough to move at least a portion of the catheter tube through the wetting chamber, in use; and wherein the wetting mechanism comprises a fluid release control component for controlling release of the fluid from the holding chamber to the wetting chamber; wherein the fluid release control component comprises a first configuration wherein it prevents release of the fluid from the holding chamber to the wetting chamber and a second configuration wherein it allows release of the fluid from the holding chamber to the wetting chamber; wherein the fluid release control component comprises a plug which is linearly moveable within the wetting mechanism between first and second positions corresponding to first and second configurations of the fluid release control component; wherein the plug is, at least initially, positioned within the wetting chamber of the wetting mechanism and is configured to be at least partly withdrawn from the wetting chamber to cause release of the fluid from the holding chamber into the wetting chamber.

Another particularly preferred embodiment provides a wetting mechanism for wetting a tube of a catheter, the wetting mechanism comprising: a housing configured to be positioned initially at or proximal to the tip end of the catheter tube, and wherein the housing comprises: a holding chamber for containing a volume of fluid therein; and a wetting chamber into which at least a portion of the catheter tube is able to be introduced and be moved therethrough to move at least a portion of the catheter tube through the wetting chamber, in use; and wherein the wetting mechanism comprises a fluid release control component for controlling release of the fluid from the holding chamber to the wetting chamber; wherein the fluid release control component comprises a first configuration wherein it prevents release of the fluid from the holding chamber to the wetting chamber and a second configuration wherein it allows release of the fluid from the holding chamber to the wetting chamber; wherein the fluid release control component comprises a plug which is linearly moveable within the wetting mechanism between first and second positions corresponding to first and second configurations of the fluid release control component; wherein the plug is, at least initially, positioned within the wetting chamber of the wetting mechanism and is configured to be at least partly withdrawn from the wetting chamber to cause release of the fluid from the holding chamber into the wetting chamber; and wherein the plug is configured such that it cannot be fully withdrawn from the wetting mechanism.

The wetting mechanism may be configured such that, in use, at least partly withdrawing the plug from the wetting mechanism causes the opening of one or more fluid outlets in the holding chamber. The one or more fluid outlets may provide a fluid communication between the holding chamber and the wetting chamber such that, in use, opening of said fluid outlet(s) may allow fluid to be released from within the holding chamber into the wetting chamber.

The wetting mechanism may be configured to retain the plug in the first and/or second position.

For example, in some embodiments the wetting mechanism may be configured to retain the plug in the first position, preventing release of the fluid from the holding chamber, unless positively acted on by a user. Advantageously, this may prevent or at least reduce the likelihood of fluid being release from the holding chamber and/or the catheter tube being exposed prematurely. This may ensure that the catheter tube is wetted at or as close as possible to the point of use to ensure the surface of the catheter tube is fully wetted. In such embodiments, the plug may be biased to the first position, and the user may be required to act against said bias to move the plug to the second position. At least a portion of the plug may abut a further component of the wetting mechanism, e.g. a lip, projection or the like from a surface of the housing preventing movement of the plug from the first position unless acted on by a user. The abutment may be provided between a frangible portion on the plug and/or on the housing configured to break upon application of a force by the user. For example, the abutment between the plug and the further component may be configured such that application of a force (e.g. the user pulling the plug away from the housing), may be sufficient to overcome said abutment, allowing the plug to be moved to the second position. The plug may "snap" or "click" in overcoming said abutment to provide tactile and/or audible feedback for the user.

In embodiments, the wetting mechanism may be configured to retain the plug in the second position, preventing the plug being returned to the first position. Advantageously, once activated, the wetting mechanism may be configured to be retained in a "used" configuration, ensuring that the catheter and wetting mechanism cannot be returned to a configuration which appears as though it has not been used—i.e. a configuration which suggests that the wetting mechanism may still be operable to wet the catheter tube (which may not be the case). This may prevent or at least reduce the likelihood of the user re-using the catheter (either mistakenly or intentionally). In such embodiments, the wetting mechanism may be configured such that, in the second configuration at least a portion of the plug is provided in an abutting relationship with a further component of the wetting mechanism (e.g. the housing) preventing further movement of the plug.

The fluid release control component may, in some embodiments, comprise a container. The container may be positioned within the holding chamber. The container may house the fluid. The container may comprise one of a sachet, blister pack, or capsule, for example.

The first configuration of the fluid release control component may correspond to a configuration wherein the container is intact, having the fluid contained therein. The second configuration of the fluid release control component may correspond to a configuration wherein the container has ruptured or has otherwise been opened to release fluid therefrom.

The wetting mechanism may be configured such that the container may be ruptured or otherwise opened, in use, through user action on the housing itself. For example, in some embodiments the housing is formed at least partly from a flexible, compressible and/or resilient material. In such embodiments, the wetting mechanism may be configured such that the container may be ruptured or otherwise opened upon a user compressing, bending and/or flexing the housing.

In further embodiments, the wetting mechanism may comprise a fluid release control component in the form of a plug, in combination with the container. In such embodiments, the wetting mechanism may be configured such that the container may be ruptured or otherwise opened, in use, through movement of the plug. For example, the wetting mechanism may be configured such that the container is compressed upon (at least partial) withdrawal of the plug, or upon rotation of the plug.

The tip end of the catheter tube may, at least initially, be disposed outside the wetting chamber. In such embodiments, the wetting mechanism may be configured such that the tip end of the catheter tube is able to be introduced into the wetting chamber and moved therethrough, in-use. For example, the wetting chamber may comprise an inlet through which the catheter tube is able to be introduced into the wetting chamber. In some embodiments the wetting chamber may comprise an outlet through which the catheter tube is able to exit the wetting chamber.

In some embodiments the wetting mechanism may be configured such that fluid released into the wetting chamber from the holding chamber is retained therein for wetting the catheter tube as it is moved therethrough, in use. For example, in some embodiments the wetting mechanism may comprise a valve arrangement. The valve arrangement may be provided at the inlet and/or outlet of the wetting chamber in order to retain fluid contained therein. The valve arrangement may be configured such that the catheter may be moved therethrough, in use.

In some embodiments the wetting mechanism is configured to be coupled to a sleeve. The wetting mechanism may be configured to be coupled to a sleeve which in turn is able to couple the wetting mechanism to a funnel, e.g. a funnel provided at or integrally formed with the distal end of the catheter tube. The wetting mechanism may be configured such that fluid released into the wetting chamber is able to flow into and along the sleeve to wet the catheter tube. For example, the wetting chamber may include an opening therein allowing fluid within the wetting chamber to flow into and along a coupled sleeve. The opening may be the inlet for the catheter tube.

In some embodiments the fluid release control component may be configured to prevent insertion of the catheter tube into and/or through the wetting chamber. For example, in some embodiments the fluid release control component may be configured to prevent insertion of the catheter tube into and/or through the wetting chamber in the first configuration—i.e. before the fluid is released from the holding chamber to the wetting chamber. Advantageously, preventing the catheter tube from being prematurely inserted and/or moved through the wetting chamber may ensure that the catheter tube is unable to be used without application of the wetting fluid. To achieve this, the fluid release control component may be configured to at least partially block an inlet for the catheter tube when in the first configuration. For example, in some embodiments a portion of the fluid release control component may be at least partially received within the inlet for the catheter tube, preventing insertion of the catheter tube into the wetting chamber. The portion of the fluid release control component may comprise a flexible, compressible and/or resilient material which may be compressed within the inlet for the catheter tube with the fluid release control component in the first configuration.

The fluid release control component may be configured such that switching (e.g. moving) the fluid release control component to a second configuration may allow insertion of the catheter tube into and/or through the wetting chamber in the second configuration. In other words, switching/moving the fluid release control component to the second configuration may both act to release fluid from within the holding chamber and remove any block on the catheter tube being inserted and/or moved through the wetting chamber.

In some embodiments the wetting mechanism comprises a wetting applicator. The wetting applicator may be positioned within the wetting chamber. The wetting applicator may be configured to hold fluid released into the wetting chamber from the holding chamber. The wetting applicator may be configured to control application of the fluid to the catheter tube, in use, as the catheter tube is moved through the wetting chamber.

One particularly preferred embodiment provides a wetting mechanism for wetting a tube of a catheter, the wetting mechanism comprising: a housing configured to be positioned initially at or proximal to the tip end of the catheter tube, and wherein the housing comprises: a holding chamber for containing a volume of fluid therein; and a wetting chamber into which at least a portion of the catheter tube is able to be introduced and be moved therethrough to move at least a portion of the catheter tube through the wetting chamber, in use; and wherein the wetting mechanism comprises a fluid release control component for controlling release of the fluid from the holding chamber to the wetting chamber; the wetting mechanism comprising a wetting applicator positioned within the wetting chamber configured to hold fluid released into the wetting chamber from the holding chamber.

Another particularly preferred embodiment provides a wetting mechanism for wetting a tube of a catheter, the wetting mechanism comprising: a housing configured to be positioned initially at or proximal to the tip end of the catheter tube, and wherein the housing comprises: a holding chamber for containing a volume of fluid therein; and a wetting chamber into which at least a portion of the catheter tube is able to be introduced and be moved therethrough to move at least a portion of the catheter tube through the wetting chamber, in use; and wherein the wetting mechanism comprises a fluid release control component for controlling release of the fluid from the holding chamber to the wetting chamber; the wetting mechanism comprising a wetting applicator positioned within the wetting chamber configured to hold fluid released into the wetting chamber from the holding chamber, wherein the wetting applicator is configured to control application of the fluid to the catheter tube, in use, as the catheter tube is moved through the wetting chamber.

The wetting applicator may comprise an absorbent material. For example, in some embodiments the wetting applicator comprises a sponge, foam or wicking material, operable to absorb the wetting fluid, in use. In further embodiments, the wetting applicator may comprise a baffle arrangement. The baffle arrangement may define a plurality of subregions of the wetting applicator each configured to hold a portion of the fluid held within the wetting applicator.

The wetting applicator may define a channel within the wetting chamber. The wetting applicator may define a channel within the wetting chamber through which the catheter tube is able to be moved through, in use. The wetting mechanism may be configured such that the catheter tube is moved in contact with the wetting applicator as it is moved through the wetting chamber (e.g. along the channel defined by the wetting applicator. In embodiments, the wetting applicator may be configured such that fluid held within the wetting applicator is able to be released, and preferably is automatically released, therefrom upon movement of the catheter tube through the wetting chamber.

Another particularly preferred embodiment provides a wetting mechanism for wetting a tube of a catheter, the wetting mechanism comprising: a housing configured to be positioned initially at or proximal to the tip end of the catheter tube, and wherein the housing comprises: a holding chamber for containing a volume of fluid therein; and a wetting chamber into which at least a portion of the catheter tube is able to be introduced and be moved therethrough to move at least a portion of the catheter tube through the wetting chamber, in use; and wherein the wetting mechanism comprises a fluid release control component for controlling release of the fluid from the holding chamber to the wetting chamber; the wetting mechanism comprising a wetting applicator positioned within the wetting chamber configured to hold fluid released into the wetting chamber from the holding chamber, wherein the wetting applicator is configured to control application of the fluid to the catheter tube, in use, as the catheter tube is moved through the wetting chamber; wherein the wetting applicator defines a channel within the wetting chamber through which the catheter tube is able to be moved through, in use, and the wetting applicator is configured such that fluid held within the wetting applicator is able to be released therefrom upon movement of the catheter tube through said channel.

The holding chamber may be configured to hold up to 0.25 ml, or up to 0.5 ml, or up to 0.75 ml, or up to 1.0 ml, or up to 1.5 ml, or up to 2.0 ml, or up to 2.5 ml, or up to 3.0 ml, or up to 4.0 ml, or up to 5.0 ml, or up to 7.5 ml, or up to 10 ml of wetting fluid, for example.

In embodiments, the housing may form a gripping element of the catheter. In use, the gripping element may be used by a user to control application of the catheter. For example, the gripping element can be used to hold the catheter tube close to the urethra to help a user guide the catheter tube without having to touch the tube itself. In embodiments, the housing may comprise a conical profile. A conical profile may be advantageous where there housing forms a gripping element of the catheter.

In embodiments wherein the fluid release control component comprises a plug, the plug may comprise a conical profile. The plug may comprise a hollow or substantially hollow interior. Where combined with a conical profile, such a plug may form a cup shape element which may assist a user with locating the catheter tube, in use. The cup can, for example, be used to locate the housing over the tip of a penis such that the catheter tube can be easily inserted into the urethra immediately after wetting.

In some embodiments, the housing and the plug both comprise a conical profile. In such embodiments, the wetting mechanism may be configured such that, together, the housing and the plug form a substantially hourglass-shaped profile. An hourglass-shaped profile may be particularly advantageous in that it may allow the user to operate the wetting mechanism—i.e. to remove (or at least partially remove) the plug from the housing using only one hand.

According to an aspect of the invention there is provided a catheter, comprising: a catheter tube having a tip end and a distal end; and the wetting mechanism of any preceding aspect operably coupled at or proximal to the tip end of the catheter tube for wetting the catheter tube, in use.

The catheter may comprise a funnel. The funnel may be provided at or proximal to the distal end of the catheter tube. The funnel may comprise a fluid outlet for the discharge of fluid from within the catheter tube.

In embodiments, the catheter comprises a sleeve. The sleeve may be positioned about the catheter tube. In embodiments, the sleeve may define an internal volume about at least a portion of the catheter tube. The sleeve may comprise a flexible material. The sleeve may be thin and readily crumpled. For example, the sleeve may be formed of a film of plastics material, which may be low-density polyethylene, for example.

The sleeve may be coupled to the wetting mechanism. For example, the sleeve may be coupled at a first end to the wetting mechanism. In such embodiments, the sleeve may be coupled at a second, opposing end to a funnel at or proximal to a distal end of the catheter tube. In this way, the sleeve may define an internal volume about the catheter tube between the wetting mechanism at or proximal to the tip end of the catheter tube, and a funnel at or proximal to a distal end of the catheter tube.

The catheter may be configured such that fluid released within the wetting chamber of the wetting mechanism is able to flow into and along the sleeve to wet the catheter tube, in use. For example, in some embodiments the housing of the wetting mechanism comprises an aperture or opening therein allowing fluid within the wetting chamber to flow into the sleeve.

The catheter may comprise a urinary catheter. The catheter may comprise a female urinary catheter, but is preferably a male urinary catheter. The catheter may comprise a single-use catheter. The catheter may comprise an intermittent urinary catheter.

The catheter tube may have a length of up to (and possibly upwards) of 35 cm. The catheter tube may be up to or at least 20 cm, up to or at least 25 cm, up to or at least 30 cm, up to or at least 35 cm, or up to or at least 40 cm, in length, for example. In embodiments, the catheter tube may be more than 40 cm in length. In preferred embodiments, the catheter tube is between 25-35 cm, in length. Male catheters typically have a catheter tube of such lengths and would be less suited to mechanisms which wet the catheter tube from the distal end (as opposed to the tip end as in the present invention), as the fluid may not adequately cover the entire length of the tube. This potentially results in the tip end being wetted last (or not at all if there is insufficient fluid), which is undesirable since the tip end will be introduced into the urethra first and is hence most likely to cause injury if inadequately wetted before use. Accordingly, the invention is particularly suited to male catheters.

The catheter tube may comprise, may be integrated with, or may be coated with a hydrophilic component. The hydrophilic component may be configured to provide a low friction surface (e.g. outer surface) of the catheter tube upon application of the wetting fluid. The hydrophilic component may comprise a hydrophilic polymer, for example.

According to an aspect of the invention there is provided a sealed packaged catheter according to the preceding aspect of the invention, wherein the wetting mechanism is operably coupled at or proximal to the tip end of the catheter tube within the sealed package.

According to an aspect of the invention there is provided a method for wetting a tube of a catheter using the wetting mechanism of any aspect described herein, the method comprising: operating the fluid release control component to cause the release of fluid from the holding chamber into the wetting chamber; and introducing the tip end of the catheter tube into the wetting chamber and moving it therethrough, thereby wetting the at least a portion of an outer surface of the catheter tube.

Operating the fluid release control component may comprise moving the fluid release control component from a first configuration wherein it prevents release of the fluid from the holding chamber to the wetting chamber to a second configuration wherein it allows release of the fluid from the holding chamber to the wetting chamber.

In some embodiments the fluid release control component comprises a plug and method may comprise at least partly withdrawing the plug from the wetting mechanism to operate the fluid release control component. The method may comprise at least partly withdrawing the plug from the wetting chamber to cause release of the fluid from the holding chamber into the wetting chamber. The method may comprise fully withdrawing the plug from the wetting mechanism to cause release of the fluid from the holding chamber to the wetting chamber.

The fluid release control component may comprise a container, such as a sachet, blister pack or capsule, for example, and the method may comprise rupturing or been opening the container to release fluid therefrom. The method may comprise compressing, bending and/or flexing the housing to rupture or otherwise open the container.

In further embodiments, the wetting mechanism may comprise a fluid release control component in the form of a plug, in combination with the container, and the method may comprise at least partly withdrawing the plug from the wetting mechanism to rupture or otherwise open the container. For example, the method may comprise compressing the container within the holding chamber upon at least partial withdrawal of the plug from the wetting mechanism.

DETAILED DESCRIPTION OF THE INVENTION

In order that the invention may be more clearly understood one or more embodiments thereof will now be described, by way of example only, with reference to the accompanying drawings, of which:

FIGS. 4A-4C are a series of further cross-sectional schematic views illustrating a further operational use of the embodiment shown in the preceding Figures;

Figure 1:
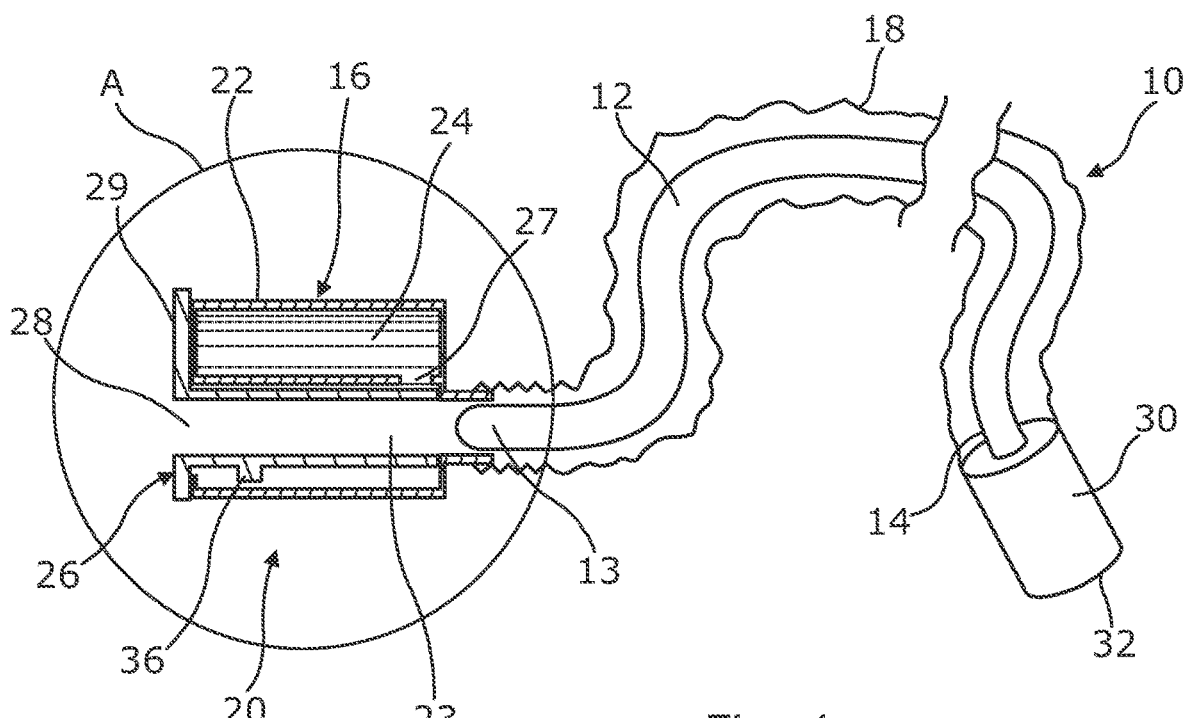
FIG. 1 is a schematic overview of a first embodiment of the invention.
Figure 2:
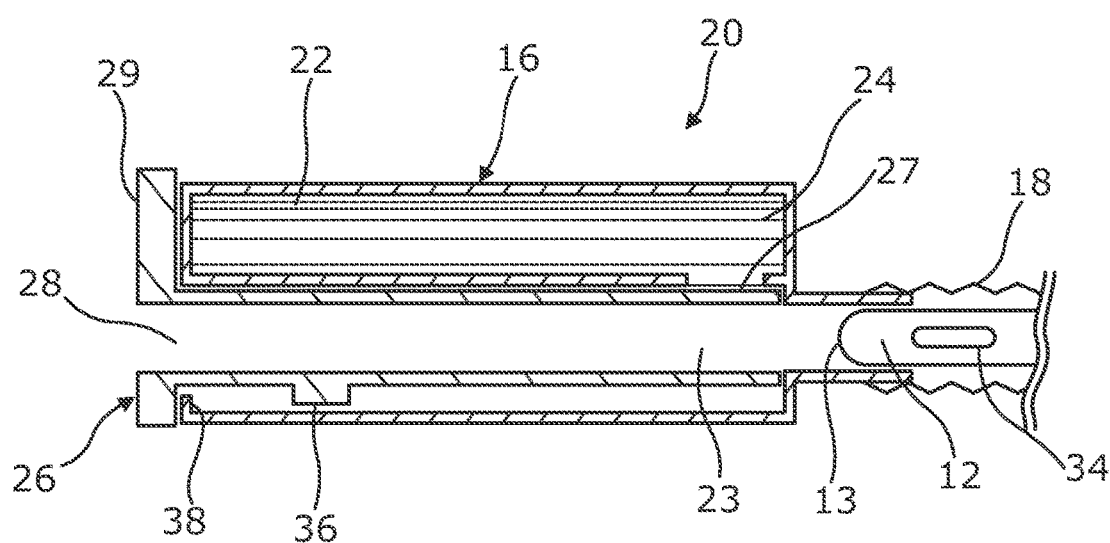
FIG. 2 is a side cross-sectional schematic view of section A in FIG. 1.

In general, the present invention relates to a catheter 10, 310, and specifically to a wetting mechanism 20, 20', 120, 220, 220', 320 configured for use to wet a tube 12, 312 of the catheter 10, 310, in use.

The Figures illustrate a series of embodiments of the invention. Where equivalent components are present between embodiments, like reference numerals have been used.

FIGS. 1-4C illustrate a first embodiment of a wetting mechanism 20 for use in wetting a tube 12 of a catheter 10.

The catheter 10 includes the catheter tube 12, with the wetting mechanism 20 provided at a tip end (proximal end) 13 of the catheter tube 12 and a funnel 30 at a distal end 14 of the catheter tube 12. A sleeve 18 is provided between the wetting mechanism 20 and the funnel 30, enclosing the catheter tube 12 therebetween. Here, the sleeve 18 is formed of a flexible material and is coupled at a first end to a housing 16 of the wetting mechanism 20 and at a second end to the funnel 30. In this way, the sleeve 18 defines an internal volume about the catheter tube 12 into which fluid may be introduced to wet the outer surface of the catheter tube 12.

As mentioned above, the catheter tube 12 has a tip end 13 and a distal end 14. The tip end 13 includes a tip for insertion of the catheter tube 12 into a canal, vessel, passageway, body cavity, etc. for removal of fluid therefrom. Here, the catheter 10 comprises a male urinary catheter 10 with the tip configured for insertion into a male patient's bladder. The tip end 13 of the catheter tube includes an aperture 34 therein for allowing for fluid to enter the interior of the catheter tube 12. The distal end 14 of the catheter tube 12 is provided within the funnel 30. Specifically, the distal end 14 of the catheter tube 12 is located within the funnel 30 and opens into the funnel 30, which defines a fluid outlet 32 which serves as an outlet for discharging fluid from within the catheter tube 12. The catheter tube 12 itself comprises a hydrophilic coating which acts to provide a low friction outer surface of the catheter tube 12 upon application of a wetting fluid.

The wetting mechanism 20 includes a tubular housing 16 positioned (at least initially) at a tip end 13 of the catheter tube 12. The housing 16 includes a holding chamber 22 which contains a volume of fluid 24 therein for wetting the catheter tube 12. In use, and as is described herein, the fluid 24 may be released from said holding chamber 22 into a wetting chamber 23 of the housing through an opening 27 within the housing 16. The wetting chamber 23 defines a separate tubular portion of the housing 16 through which at least a portion of the catheter tube 12 is able to be introduced and be moved therethrough. Accordingly, by releasing the fluid 24 into the wetting chamber 23, and subsequently moving the catheter tube 12 through the wetting chamber 23, an outer surface of the catheter tube 12 may be wetted using the fluid 24.

The wetting mechanism 20 comprises a fluid release control component in the form of a plug 26. As is described herein, the plug 26 is configured to control release of the fluid 24 from the holding chamber 22 to the wetting chamber 23. In the illustrated embodiment, the plug 26 is substantially cylindrical and defines an outlet 28 of the housing 16 through which, in use, the catheter tube 12 can be moved, although other profiles are equally applicable. As shown in FIGS. 1-3A, the plug 26 is initially located within the wetting chamber 23 with a portion of the plug 26 blocking opening 27. This is herein referred to as a first position or first configuration of the plug 26, corresponding to a position wherein the fluid 24 is prevented from being released from the wetting chamber 23. A lip 29 is provided at an end of the plug 26 which defines an interaction point for the user, specifically for the user to grip the lip 29 to provide leverage for moving the plug 26.

Figure 3A:
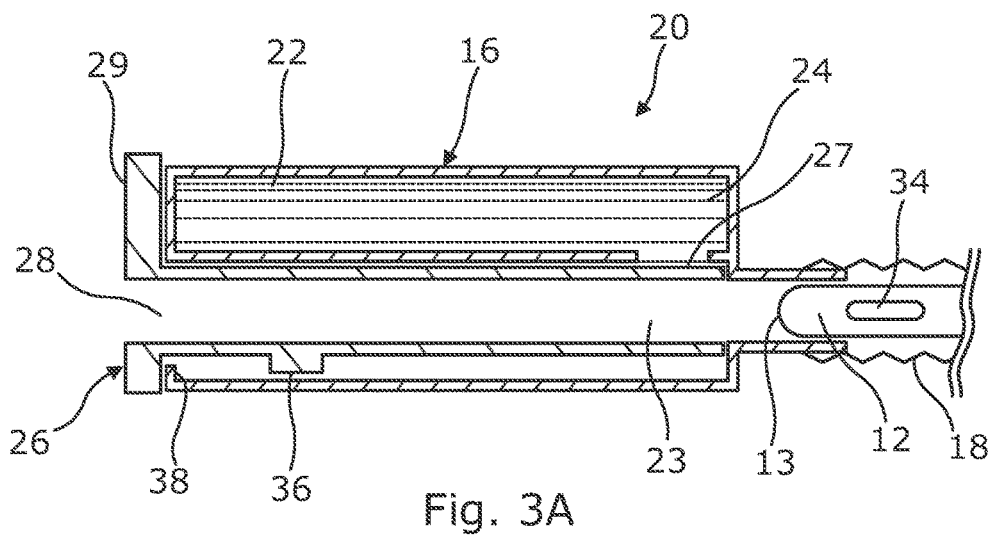
FIGS. 3A-3C are a series of cross-sectional schematic views illustrating the operational use of the embodiment of the preceding Figures.
Figure 3B:
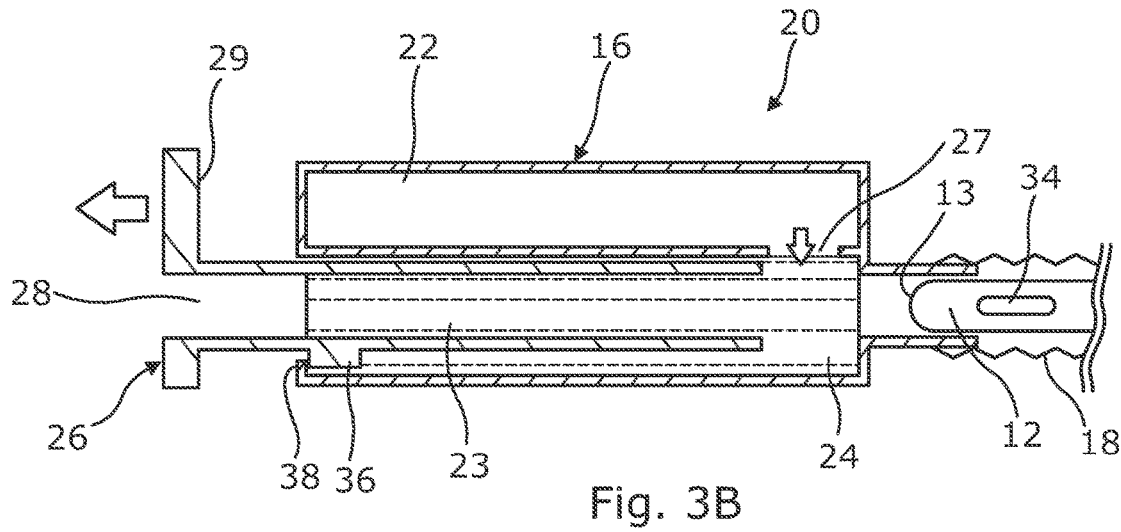
Figure 3C:
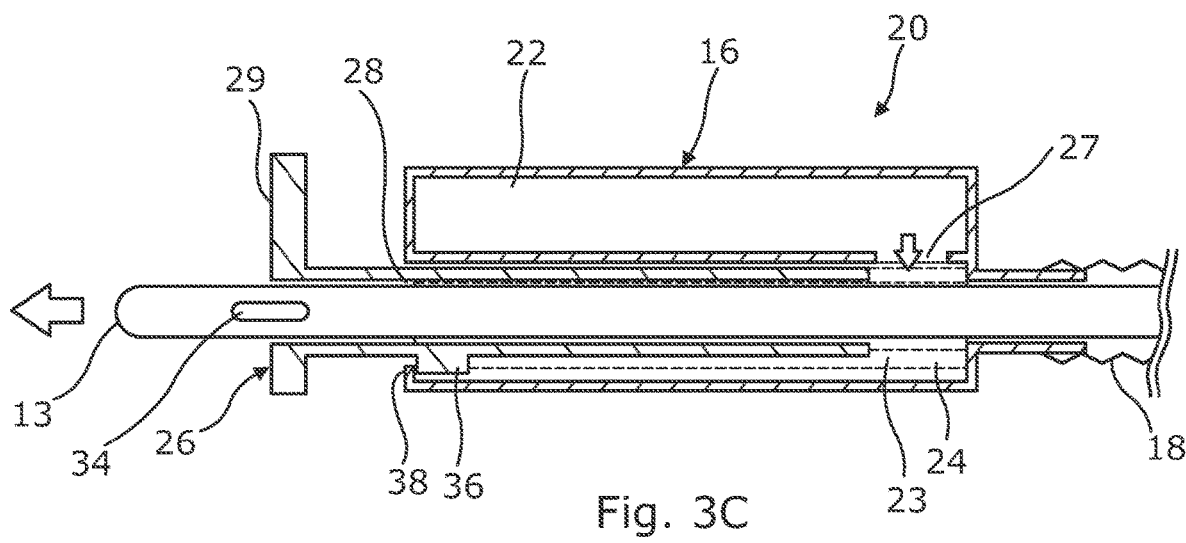

FIGS. 3A-3B illustrate the operational use of the wetting mechanism 20 in a horizontal orientation. As set out above, initially the wetting mechanism 20 is provided in the first configuration with the plug 26 in a first position blocking the opening 27 (FIG. 3A). In order to activate the wetting mechanism 20, the plug 26 is partially displaced from (i.e. pulled out from) the wetting chamber 23 to a second position (FIG. 3B). In doing so, the plug 26 is moved to a position where the opening 27 is no longer blocked, allowing the fluid 24 to be released from the holding chamber 22 into the wetting chamber 23. Spillage (or at least major spillage) of fluid through the outlet 28 of the housing 16 is prevented due to the relatively small volume of wetting fluid 24 provided (approximately 2.5 ml), and the surface tension of the fluid 24 itself. A notch 36 is provided on an outer circumferential surface of the plug 26 to define the extent to which the plug 26 can be removed from the wetting chamber 23. Specifically, the notch 36 provides a point of contact between the plug 26 and a circumferentially inwardly extending flange 38 at the end of the housing 16.

Subsequently, the catheter tube 12 may be moved through the wetting chamber 23, bringing the catheter tube 12 into contact with the wetting fluid 24 and hence wetting an outer surface of the catheter tube 12. Once the tip end 13 of the catheter tube 12 is moved beyond the lip 29 in the plug 26, and out through an outlet 28 of the housing 16, the tip end 13 then becomes exposed for insertion by the user. The housing 16 then acts as a gripping element for the user to direct the catheter tube 12, in use, as the user may then use the housing 16 to easily direct the exposed tip end 13 of the catheter tube 12 without contacting the tube 12 directly.

FIGS. 4A-4C illustrate a further operational use of the wetting mechanism 20 shown in the preceding figures. Specifically, starting at FIG. 4A, the housing 16 is held in a vertical orientation with the plug 26 in a first position preventing release of the wetting fluid 24 from the holding chamber 22. The plug 26 is then pulled out from the wetting chamber 23 in the same manner as discussed above to unblock opening 27 and thereby release the wetting fluid 24 (FIG. 4B). With the housing 16 held in this orientation, the wetting fluid 24 is released into the wetting chamber 23 and subsequently into the sleeve 18 and about the exterior surface of the catheter tube 12. In this way, the wetting fluid 24 is allowed to run along the sleeve 18, thereby wetting the catheter tube 12. The catheter tube 12 may then be moved through the wetting chamber 23 and past the lip 29 in the plug 26 to expose the tip end 13 for insertion by the user. Again, the housing 16 acts as a gripping element for the user to direct the catheter tube 12, in use, as it is expelled through the housing 16 and introduced into the urethra.

Figure 5A:
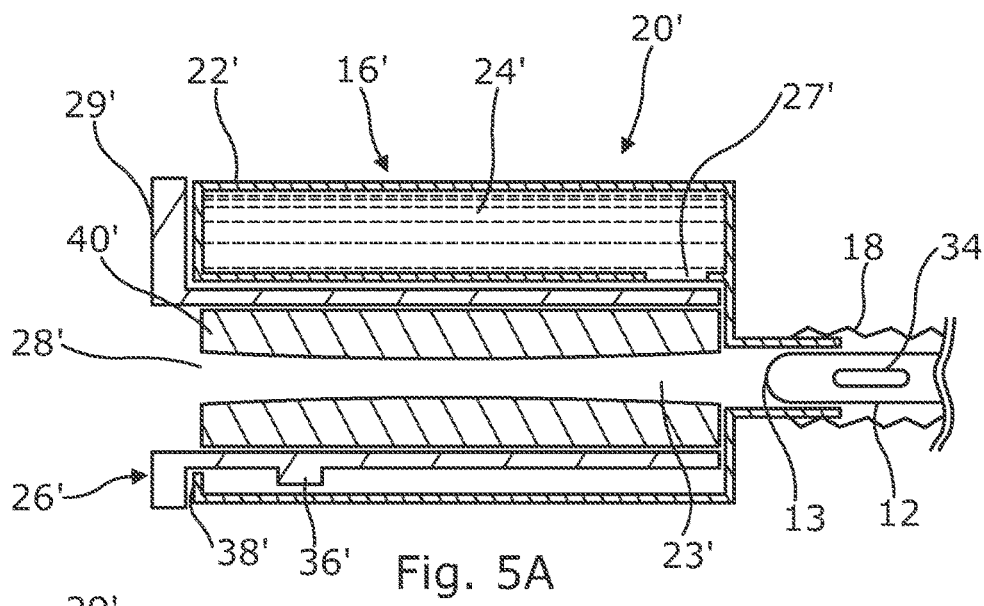
FIGS. 5A-5C are a series of cross-sectional schematic views illustrating the operational use of a second embodiment of the invention.
Figure 5B:
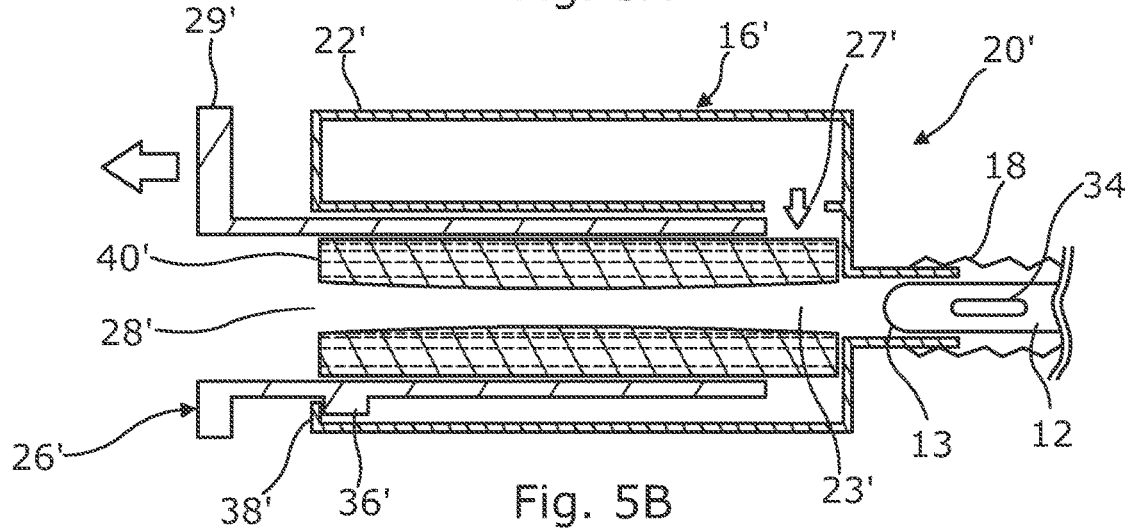
Figure 5C:
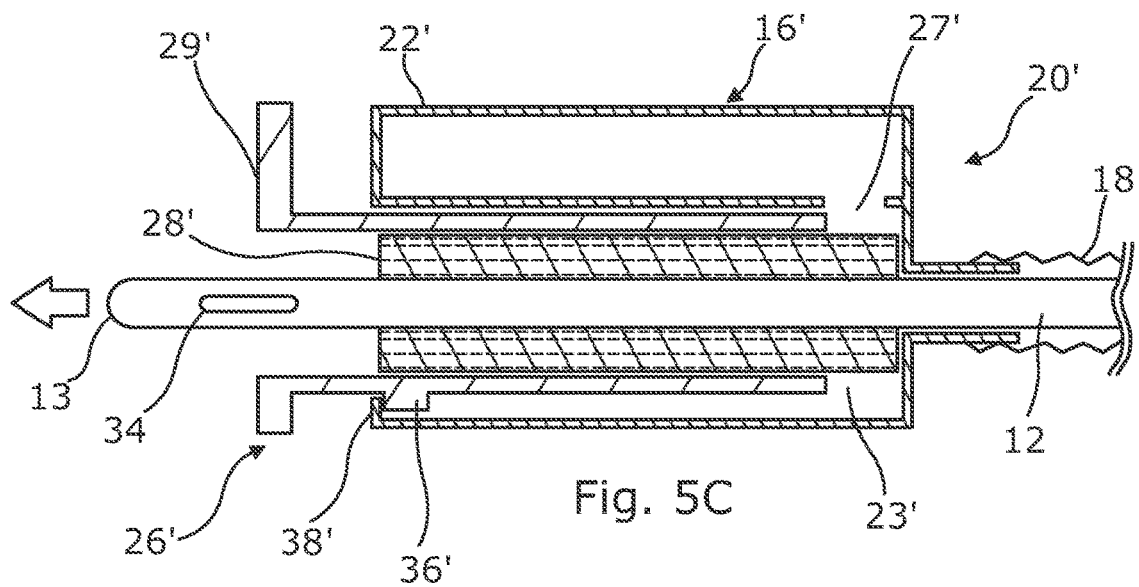

A variant of wetting mechanism 20 is shown in FIGS. 5A-5C. Specifically, these figures show a wetting mechanism 20' configured in substantially the same way as wetting mechanism 20 shown in the preceding Figures. Wetting mechanism 20' differs in that it additionally includes a wetting applicator in the form of a foam conduit 40' positioned within the wetting chamber 23'. As is discussed in detail herein, the foam conduit is configured to hold fluid released into the wetting chamber 23' from the holding chamber 22' and is configured to control application of the fluid to the catheter tube 12, in use, as the catheter tube 12 is moved through the wetting chamber 23'.

Wetting mechanism 20' functions in essentially the same way as wetting mechanism 20, with a fluid release control component provided in the form of a plug 26' movable between two positions to control release of the wetting fluid 24' from the holding chamber 22'. Here, upon movement of the plug 26' to the second position, thereby unlocking the opening 27', the fluid 24' contained within the holding chamber 22' is released onto the foam conduit 40'. The foam conduit 40' stores the fluid 24' released onto it for subsequent application to the catheter tube 12. Specifically, the foam conduit 40' defines a channel within the wetting chamber 23' through which the catheter tube 12 is able to move through and be brought into contact with the foam conduit 40'. The foam conduit 40' is configured such that fluid held therein is released upon movement of the catheter tube 12 through the defined channel by virtue of the catheter tube 12 coming into contact with the foam conduit 40' and applying a pressure thereto. A wetting applicator of this type may advantageously ensure that the wetting fluid 24' is applied evenly across the outer surface of the catheter tube 12, and reduce the prospect of any spillage.

Figure 6A:
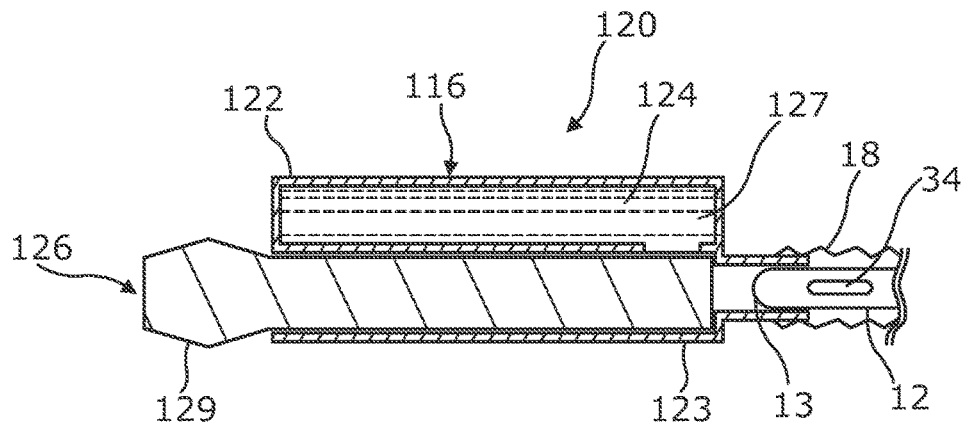
FIGS. 6A-6C are a series of cross-sectional schematic views illustrating the operational use of a third embodiment of the invention.
Figure 6B:
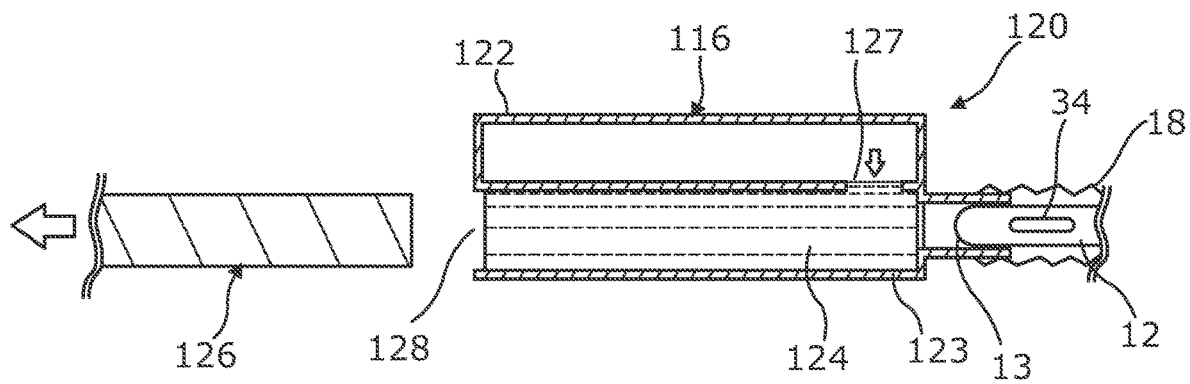
Figure 6C:
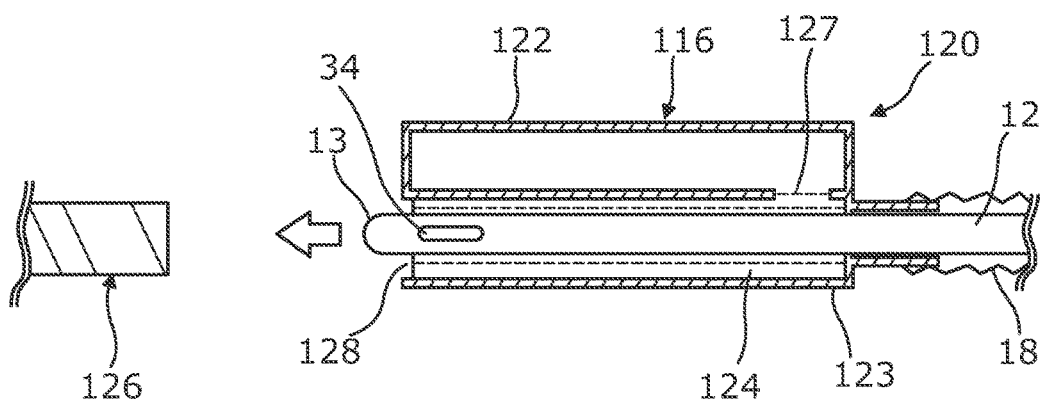

FIGS. 6A-6C illustrate a further embodiment of a wetting mechanism 120 according to the invention, for wetting an outer surface of the catheter tube 12.

As with wetting mechanism 20, the wetting mechanism 120 comprises a housing 116 positioned (at least initially) at a tip end 13 of the catheter tube 12. The housing 116 again includes a holding chamber 122 which contains a volume of fluid 124 therein for wetting the catheter tube 12, and a wetting chamber 123 into which the fluid 124 may be released—specifically through an opening 127 within the housing 116. The wetting chamber 123 again defines a separate portion of the housing 116 through which at least a portion of the catheter tube 12 is able to be introduced and be moved therethrough.

Wetting mechanism 120 differs in that the fluid release control component in this embodiment is provided in the form of a plug 126 which must be fully removed from the chamber 123 in order to release the fluid 124 and allow the catheter tube 12 to be moved through the housing 116. Specifically, the plug 126 is initially provided in the position shown in FIG. 6A, with the plug 126 provided almost entirely within the wetting chamber 123 of the housing 116. In this position, the opening 127 in the housing 116 is blocked preventing the release of the fluid 124 from the holding chamber 122. This is referred to herein as a first position or first configuration of the plug 126. In use, the plug 126 is removed from the wetting chamber 123 to release the fluid 124 into the wetting chamber 123. This is performed by a user gripping and interaction region 129 on the plug 126 and pulling the plug 126 from the wetting chamber 123 (as shown in FIG. 6B). Removal of the plug 126 opens an outlet 128 in the housing 116 through which the catheter tube 12 may be exposed, in use. As with wetting mechanism 20, catheter tube 12 may then be moved through the wetting chamber 123 through the outlet 128 to both wet the outer surface of the catheter tube 12 and expose the tip end 13 for insertion by the user. Again, the housing 116 acts as a gripping element for the user to direct the catheter tube 12, in use.

Figure 7A:
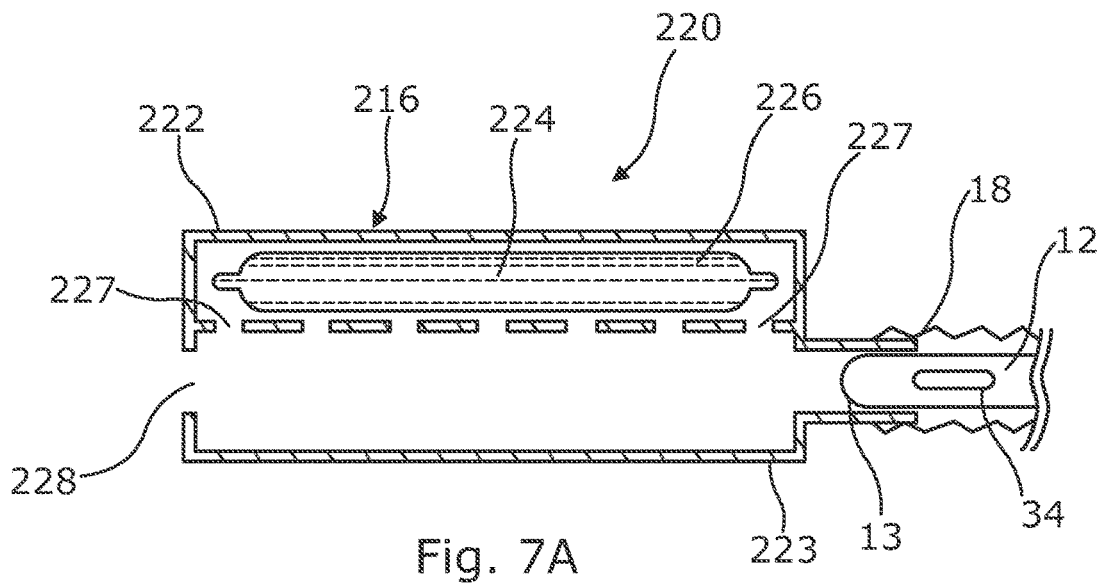
FIGS. 7A-7C are a series of cross-sectional schematic views illustrating the operational use of a fourth embodiment of the invention.
Figure 7B:
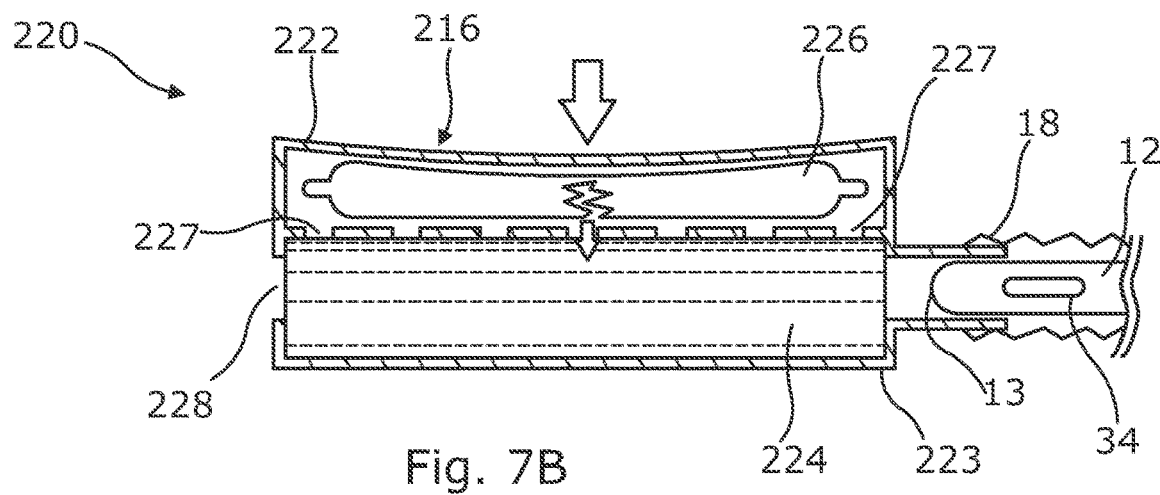
Figure 7C:
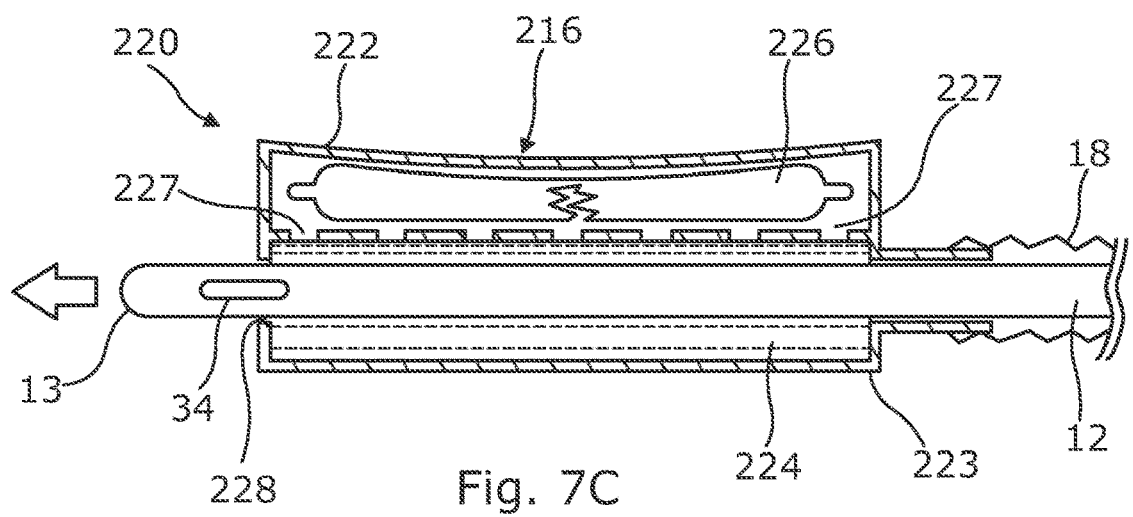

FIGS. 7A-7C illustrate a further embodiment of a wetting mechanism 220 according to the invention, for wetting an outer surface of the catheter tube 12.

As with wetting mechanisms 20 and 120, the wetting mechanism 220 comprises a housing 216 positioned (at least initially) at a tip end 13 of the catheter tube 12. The housing 216 again includes a holding chamber 222 which contains a volume of fluid 224 therein for wetting the catheter tube 12, and a wetting chamber 223 into which the fluid 124 may be released—specifically through openings 227 within the housing 216. The wetting chamber 223 again defines a separate portion of the housing 216 through which at least a portion of the catheter tube 12 is able to be introduced and be moved therethrough.

Wetting mechanism 220 differs in that the fluid release control component in this embodiment is provided in the form of a plug container of fluid, specifically a sachet 226 which must be ruptured in order to release the fluid 224 therefrom and into the wetting chamber 223. Specifically, the sachet 226 is initially provided in the configuration shown in FIG. 7A—i.e. intact, with the fluid contained therein. In use, the sachet 226 is ruptured through a user applying an external force to the housing 216, i.e. by squeezing the housing 216 (as shown figuratively in FIG. 7B), which may be formed of a deformable material, or with a deformable region that can be squeezed. Rupture of the sachet 226 causes the fluid contained therein to be released into the wetting chamber 223 through openings 227 provided within the housing 216. As with wetting mechanisms 20, 120, the catheter tube 12 may then be moved through the wetting chamber 223 through an outlet 128 at a distal end of the housing 216 to both wet the outer surface of the catheter tube 12 expose the tip end 13 for insertion by the user. Again, the housing 216 acts as a gripping element for the user to direct the catheter tube 12, in use.

Figure 8A:
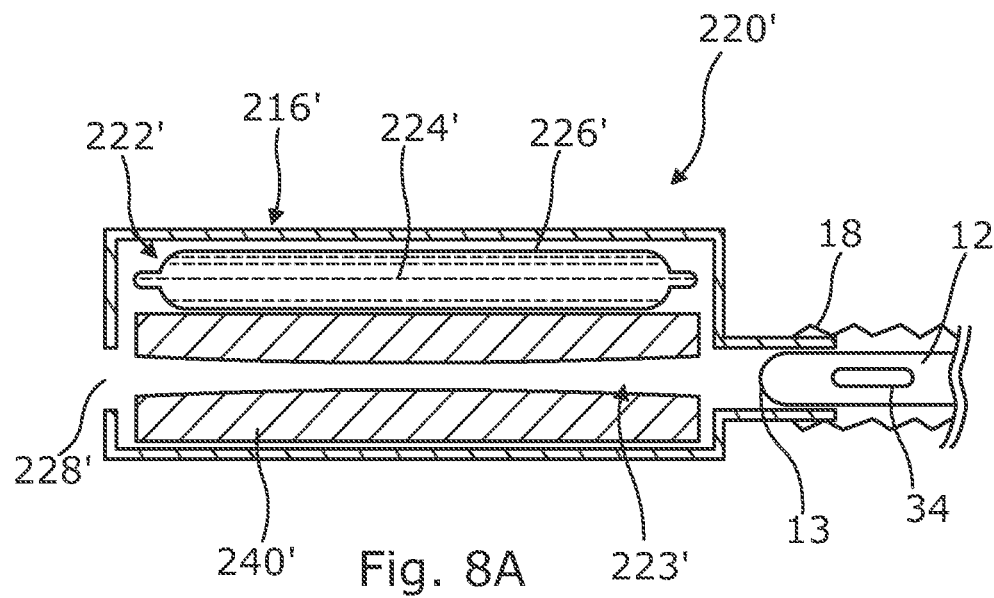
FIGS. 8A-8C are a series of cross-sectional schematic views illustrating the operational use of a fifth embodiment of the invention.
Figure 8B:
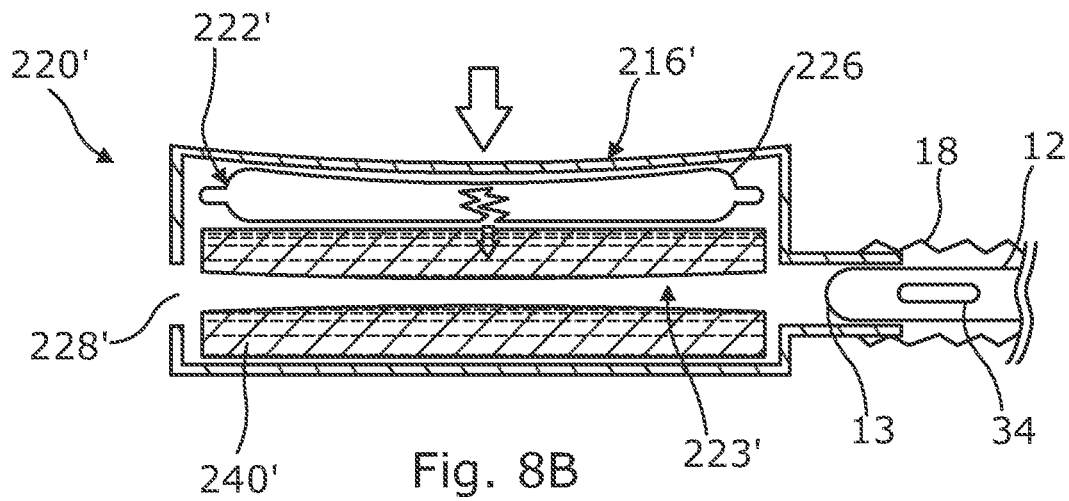
Figure 8C:
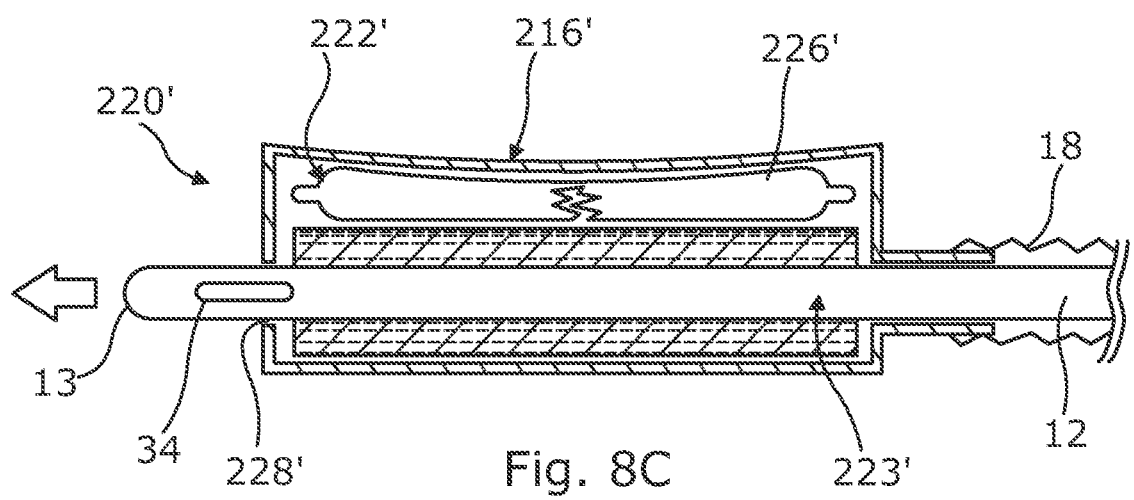

A variant of wetting mechanism 220 is shown in FIGS. 8A-8C. Wetting mechanism 220' differs in that it additionally includes a wetting applicator in the form of a foam conduit 240'. As with foam conduit 40', the foam conduit 240' is configured to hold fluid released thereon from the holding chamber 222' and is configured to control application of the fluid to the catheter tube 12, in use, as the catheter tube 12 is moved through the housing 216'. Wetting mechanism 220' functions in essentially the same way as wetting mechanism 220, with a fluid release control component provided in the form of a rupturable sachet 226' controlling the release of the wetting fluid 224'. In use, rupturing the sachet 226' causes the fluid 224' contained therein to be released onto the foam conduit 240' which stores the fluid 224' for subsequent application to the catheter tube 12. Here, the sachet 226' defines the holding chamber 222' with the foam conduit 240' defining the wetting chamber 223' through which the catheter tube 12 may be moved, in use.

Figure 9:
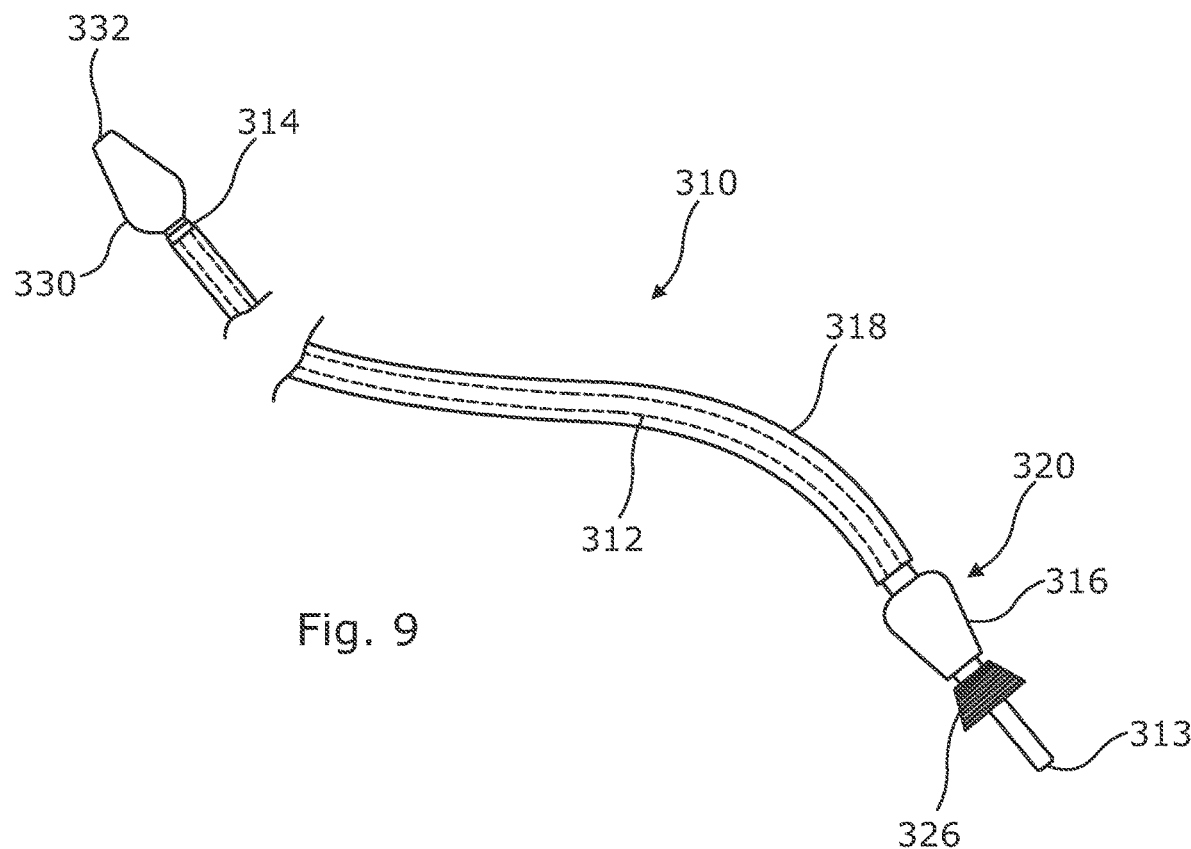
FIG. 9 is a perspective view of a sixth embodiment of the invention.
Figures 10A, 10B:
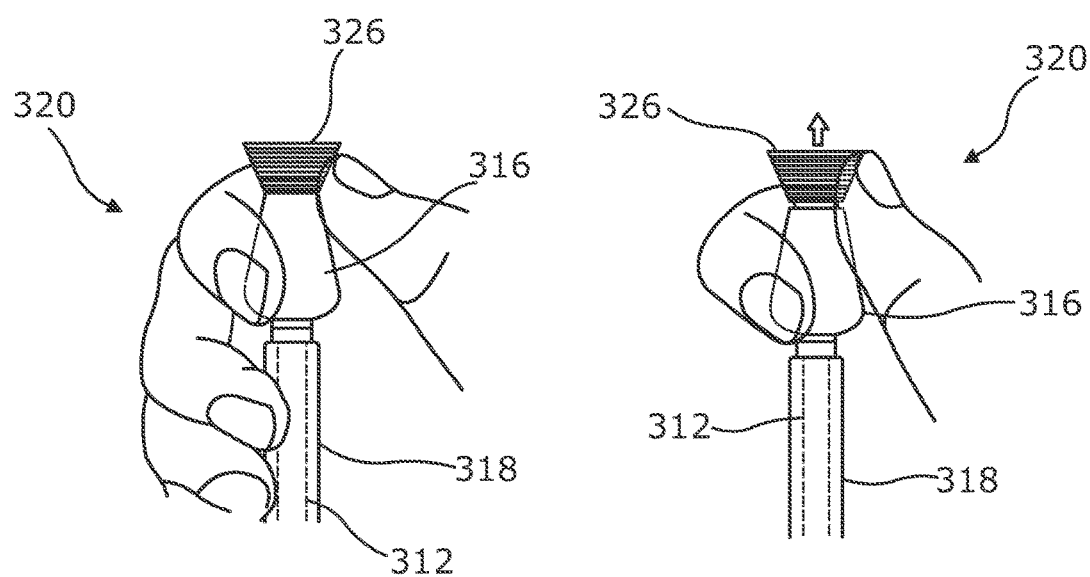
FIGS. 10A-10B are a pair of side views illustrating the operational use of the embodiment shown in FIG. 9.

FIGS. 9-10B illustrate further embodiments of a catheter 310 and wetting mechanism 320 operable to wet a tube 312 of the catheter 310, in use.

As with catheter 10, the catheter 310 includes the catheter tube 312, with the wetting mechanism 320 provided at a tip end 313 of the catheter tube 312 and a funnel 330 at a distal end 314 of the catheter tube 312. A sleeve 318 is provided between the wetting mechanism 320 and the funnel 330, enclosing the catheter tube 12 therebetween.

The tip end 313 of the catheter 310 includes a tip for insertion of the catheter tube 312 into a canal, vessel, passageway, body cavity, etc. for removal of fluid therefrom. Here, the catheter 310 comprises a male urinary catheter 310 with the tip configured for insertion into a male patient's bladder. The distal end 314 of the catheter tube 312 is provided within the funnel 330. Specifically, the distal end 314 of the catheter tube 312 is located within the funnel 330 and opens into the funnel 330 which defines a fluid outlet 332 which serves as an outlet for discharging fluid from within the catheter tube 312. The funnel 330 is shaped to aid the user's control over the direction of discharge of the fluid from the catheter tube 312. The catheter tube 312 itself comprises a hydrophilic coating which acts to provide a low friction outer surface of the catheter tube 312 upon application of a wetting fluid.

The wetting mechanism 320 is similar in configuration to wetting mechanism 20 described herein, and may be of the nature of, with the same features as, any of the embodiments of FIGS. 1-5C or 7A-8C. It includes a housing 316 positioned (at least initially) at the tip end 313 of the catheter tube 312. The housing 316 includes a holding chamber (not shown) which contains a volume of fluid therein for wetting the catheter tube 312. In use, and as is described herein, the fluid may be released from said holding chamber into a wetting chamber (not shown) of the housing 316 under the operation of a plug 326. As with the other embodiments described herein, by releasing the fluid into the wetting chamber, and subsequently moving the catheter tube 312 through the wetting chamber, an outer surface of the catheter tube 312 may be wetted using the fluid. The plug 326 is moveable from the position shown in FIG. 10A (a first position) to the position shown in FIG. 10B (a second position) to release the fluid from the holding chamber. Specifically, movement of the plug 326 between these positions may unblock an opening within the housing 316 or rupture a sachet, for example, to allow for the fluid to be released from the holding chamber.

In this embodiment, the plug 326 comprises a conical cross section, with a ridged exterior surface defining an interaction surface for the user. The housing 316 is also substantially conical in profile, and is positioned in such a way to define an hourglass-shaped configuration of the housing 316 and plug 326. This arrangement is particularly beneficial as it may allow for operation of the plug 326 using only one hand, as shown in FIGS. 10A and 10B. Specifically, and as shown in these Figures, the user may grip the housing 316 and plug 326 between their thumb and forefinger, before using their thumb to push or "pop" the plug 326 upwards (in the orientation shown in the Figures) to release the fluid. Moreover, the conical plug 326 has a cup like end, which eases location of the housing 316 over the tip of the penis to aid insertion of the catheter tube 312 into the urethra, in use.

In a variant, the fluid release control component (e.g. the plug 26, 126, 326) may alternatively be rotatable between first and second positions/configurations to control the release of the wetting fluid. For example, rotation of the plug 26, 126, 326 (rather than linear movement) may align an opening in the plug to unblock an opening 27, 127 or valve in the housing 16, 116, 316 allowing for the release of the wetting fluid.

In a variant, the wetting mechanism (e.g. mechanism 20) may be configured to retain the plug 26 in the first and/or second position. For example, the wetting mechanism 20 may be configured to retain the plug 26 in the first position, preventing release of the fluid from the holding chamber 22 unless positively acted on by a user. This may be provided, for example, in the form of an abutment between a frangible portion on the plug 26 and/or on the housing 16 configured to break upon application of a force by the user. In this way, the plug 26 may "snap" or "click" in overcoming said abutment to provide tactile and/or audible feedback for the user. The wetting mechanism 20 may be configured such that, in the second position at least a portion of the plug 26 is provided in an abutting relationship with a further component of the wetting mechanism (e.g. the housing 16) preventing further movement of the plug 26 and thereby preventing the plug 26 being returned to the first position.

In a variant, the wetting mechanism 20, 20', 120, 220, 320 of the invention may include both a plug (e.g. plug 26) and rupturable container (e.g. sachet 226). Here, the wetting mechanism may be configured such that the container may be ruptured through compression on the container upon (at least partial) withdrawal of the plug, or upon rotation of the plug.

In a variant, the housing (e.g. housing 16) may include a valve arrangement or the like preventing the wetting fluid from being released from the housing. For example, the housing can include a valve arrangement at an inlet and/or an outlet. The valve arrangement may be configured to allow the catheter tube 12, 312 to be moved therethrough.

In a variant, the fluid release control component (e.g. the plug 26, 126, 326 can be configured to prevent insertion of the catheter tube into and/or through the wetting chamber when in the first position—i.e. before the fluid is released from the holding chamber to the wetting chamber. This may, for example, involve the fluid release control component at least partially blocking an inlet for the catheter tube 12, 312.

In a variant, the wetting applicator can comprise a sponge or wicking material, operable to absorb the wetting fluid, in use, or may comprise a baffle arrangement.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

The one or more embodiments are described above by way of example only. Many variations are possible without departing from the scope of protection afforded by the appended claims.

The invention claimed is:

1. A wetting mechanism for wetting a tube of a catheter, the wetting mechanism comprising:
   a housing configured to be positioned initially at or proximal to a tip end of the catheter tube, and wherein the housing comprises:
   a holding chamber for containing a volume of fluid therein; and
   a wetting chamber configured to receive at least a portion of the catheter tube such that the catheter tube is moveable therethrough to move at least a portion of the catheter tube through the wetting chamber, in use; and
   wherein the wetting mechanism comprises a fluid release control component for controlling release of the fluid from the holding chamber to the wetting chamber;
   wherein the fluid release control component comprises a first configuration that prevents release of the fluid from the holding chamber to the wetting chamber and a second configuration that allows release of the fluid from the holding chamber to the wetting chamber:
   wherein the fluid release control component comprises a plug which is linearly moveable within the wetting mechanism between first and second positions corresponding to first and second configurations of the fluid release control component:
   wherein the plug is configured to be at least partly withdrawn from the wetting mechanism to cause release of fluid from the holding chamber into the wetting chamber:
   wherein the plug is configured such that it cannot be fully withdrawn from the wetting mechanism:
   wherein the plug is substantially cylindrical and defines an outlet configured to allow the tube of the catheter to move there through.

2. A wetting mechanism as claimed in claim 1, wherein the plug is, at least initially, positioned within the wetting chamber of the wetting mechanism and is configured to be at least partly withdrawn from the wetting chamber to cause release of the fluid from the holding chamber into the wetting chamber.

3. A wetting mechanism as claimed in claim 1, wherein the tip end of the catheter tube is positionable outside the wetting chamber and the wetting mechanism is configured such that the tip end of the catheter tube is introduceable into the wetting chamber and moveable therethrough.

4. A wetting mechanism as claimed in claim 1, wherein the wetting mechanism is configured to release fluid into the wetting chamber from the holding chamber for wetting the catheter tube as the catheter tube moves therethrough.

5. A wetting mechanism as claimed in claim 4, comprising a valve arrangement provided at an inlet and/or outlet of the wetting chamber in order to retain fluid contained therein.

6. A wetting mechanism as claimed in claim 1, configured to be coupled to a sleeve, and configured to release fluid into the wetting chamber to flow into and along a coupled sleeve to wet the catheter tube.

7. A wetting mechanism as claimed in claim 1, wherein the fluid release control component is configured to prevent insertion of the catheter tube into and/or through the wetting chamber in the first configuration, and is configured to allow insertion of the catheter tube into and/or through the wetting chamber in the second configuration.

8. A wetting mechanism of claim 1, comprising a wetting applicator positioned within the wetting chamber configured to hold fluid released into the wetting chamber from the holding chamber.

9. A wetting mechanism as claimed in claim 8, wherein the wetting applicator is configured to control application of the fluid to the catheter tube as the catheter tube is moved through the wetting chamber.

10. A wetting mechanism as claimed in claim 9, wherein the wetting applicator defines a channel within the wetting chamber through which the catheter tube is configured to be moved through and the wetting applicator is configured such that fluid held within the wetting applicator is releasable therefrom upon movement of the catheter tube through said channel.

11. A wetting mechanism as claimed in claim 1, wherein the housing forms a gripping element for the catheter.

12. A wetting mechanism as in claim 1, comprising a sealed package, wherein the wetting mechanism is operably coupled at or proximal to a tip end of a catheter tube within the sealed package.

* * * * *